United States Patent [19]
Borthwick et al.

[11] Patent Number: 5,100,896
[45] Date of Patent: Mar. 31, 1992

[54] CARBOCYCLIC ANALOGUES OF 7H-1,2,3-TRIAZOLO [4,5-D]PYRIMIDINE FURANOSIDES

[75] Inventors: Alan D. Borthwick, London; Keith Biggadike, Greenford; Barrie E. Kirk, Ickenham; Richard Storer, Pinner; Niall G. Weir, Wembley; Anthony D. Baxter, Iver Heath; Chi L. Mo, Greenford, all of England

[73] Assignee: Glaxo Group Limited, London, England

[21] Appl. No.: 556,262

[22] Filed: Jul. 23, 1990

[30] Foreign Application Priority Data

Jul. 24, 1989 [GB] United Kingdom ............... 8916854
May 17, 1990 [GB] United Kingdom ............... 9011053

[51] Int. Cl.$^5$ ................. C07D 471/02; A61K 31/505
[52] U.S. Cl. .................................... 514/258; 544/254; 544/229; 544/323; 544/277
[58] Field of Search ..................... 544/254; 514/258

[56] References Cited

U.S. PATENT DOCUMENTS

| | | | |
|---|---|---|---|
| 4,138,562 | 2/1979 | Vince | 544/254 |
| 4,268,672 | 5/1981 | Vince | 544/265 |
| 4,543,255 | 9/1985 | Shealy et al. | 544/254 |
| 4,605,659 | 8/1986 | Verbeyden et al. | 544/265 |
| 4,714,701 | 12/1987 | Beauchamp | 544/254 |
| 4,728,736 | 3/1988 | Shealy et al. | 544/254 |
| 4,857,531 | 8/1989 | Borthwick et al. | 544/276 |

FOREIGN PATENT DOCUMENTS

| | | |
|---|---|---|
| 0215759 | 3/1987 | European Pat. Off. |
| 0236935 | 9/1987 | European Pat. Off. |
| 0277599 | 8/1988 | European Pat. Off. |
| 0304889 | 3/1989 | European Pat. Off. |
| 0345076 | 12/1989 | European Pat. Off. |

OTHER PUBLICATIONS

Shealy et al., "Synthesis and Antiviral Evaluation of Carbocyclic Analogues of 2-Amino-6-Substituted-Purine 3'-Deoxyribofuranosides", J. Med. Chem., vol. 30, No. 6, (1987) pp. 1090–1094.

Shealy et al., "Synthesis and Antiviral of Carbocyclic Analogues of 2'-Deoxyribofuranosides of 2-Amino-6-Substituted-Purines and of 2-Amino-6-Substituted-8-Azapurines", J. Med. Chem., vol. 27, No. 11, (1984) pp. 1416–1421.

Vince et al., "Synthesis and Antiviral Activity of Carbocyclic Analogues of Xylofuranosides of 2-Amino-6-Substituted-Purines and 2-Amino-6-Substituted-8-Azapurines", J. Med. Chem., vol. 30, No. 11, (1987) pp. 2026–2030.

Vince et al., "Synthesis and Anti-HIV Acitivity of Carbocyclic 2',3'-Didehydro-2',3'-Dideoxy 2,6-Disubstituted Purine Nucleosides", J. Med. Chem., vol. 33, No. 1, (1990) pp. 17–21.

Patterson and Vince, "Synthesis and Biological Evaluation of Carbocyclic Analogues of Lyxofuranosides of 2-Amino-6-Substituted-Purines and 2-Amino-6-Substituted-Purines and 2-Aminio-6-Substituted-8-Azapurines", J. Med. Chem., vol. 33, No. 4, (1990) pp. 1214–1219.

Shealy et al., "Synthesis and Antiviral Evaluation of Carbocyclic Analogues of Ribofuranosides of 2-Amino-6-Substituted-Purines and of 2-Amino-6-Substituted-8-Azapurines", J. Med. Chem., vol. 27, No. 5, (1984) pp. 670–674.

Shealy et al., "Carbocyclic Analogs of Guanosine and 8-Azaguanosine", J. Pharm. Sci., vol. 62, No. 9, (1973) pp. 1432–1434.

Lee et al., "Carbocyclic Analogs of Arabinosylpurine Nucleosides", J. Pharm. Sci., vol. 69, No. 9, (1980) pp. 1019–1021.

Vince et al., "Facile Synthesis of Carbocyclic Lyxo- and Ribonucleosides", J. Org. Chem., vol. 45, No. 3, (1980) pp. 531–533.

Shealy et al., "Cyclopentyl Derivatives of 8-Azahypoxanthine and 8-Azaadenine, Carbocyclic Analogs of 8-Azainosine and 8-Azaadenosine(1)", J. Het. Chem., vol. 10, No. 4, (1973) pp. 601–605.

Shealy et al., "Synthesis and Antiviral Activity of the Carbocyclic Analogues of 5-Ethyl-2'-Deoxyuridine and of 5-Ethynyl-2'-deoxyuridine", J. Med. Chem., vol. 29, No. 1, (1986) pp. 79–84.

Primary Examiner—Donald G. Daus
Attorney, Agent, or Firm—Bacon & Thomas

[57] ABSTRACT

The present invention provides a compound of formula (I)

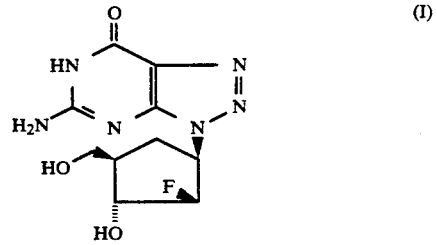

and salts and solvates and pharmaceutically acceptable derivatives thereof, and describes processes for their preparation, pharmaceutical compositions containing them and their use in the treatment of viral diseases, especially those caused by the Herpetoviridae.

9 Claims, No Drawings

CARBOCYCLIC ANALOGUES OF 7H-1,2,3-TRIAZOLO [4,5-D]PYRIMIDINE FURANOSIDES

This invention relates to new carbocyclic nucleoside derivatives having activity against viruses, especially Herpetoviridae, to processes for their preparation, to pharmaceutical compositions containing them and to their use in medicine.

Existing treatments for viral infections include the administration of chemical compounds which are nucleoside analogues, for example 2'-deoxy-5-iodouridine, 9-(2-hydroxyethoxymethyl)guanine and 9-β-D-arabinofuranosyladenine. In UK Patent Specification No. 2179349A we describe antiviral fluoro-substituted carbocyclic analogues of nucleosides wherein the nucleoside base is a substituted purine base. Such compounds have activity against strains of herpes simplex virus types I and II. There is however a need for compounds with good antiviral activity coupled with lower levels of cytotoxicity.

We have now found that the new fluoro substituted carbocyclic analogues of nucleosides of formula (I) below have good activity against viruses, especially Herpetoviridae including strains of herpes simplex virus type 1 (HSV-1), herpes simplex virus type 2 (HSV-2) and varicella-zoster virus (VZV), whilst having a low level of cytotoxicity.

Thus, according to one aspect, the invention provides a compound of formula I

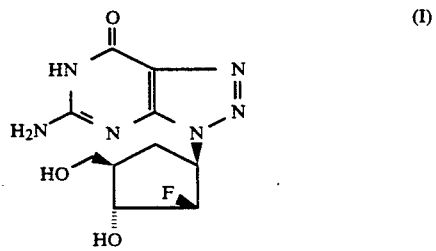

and salts, solvates and pharmaceutically acceptable derivatives thereof.

It will be appreciated that, for pharmaceutical use, the salts referred to above will be the physiologically acceptable salts, but other salts may find use, for example in the preparation of compounds of formula (I) and the physiologically acceptable salts thereof.

Suitable physiologically acceptable salts of the compound of formula (I) include acid addition salts formed with organic or inorganic acids (for example hydrochlorides, hydrobromides, sulphates, phosphates, benzoates, naphthoates, hydroxynaphthoates, p-toluenesulphonates, methanesulphonates, sulphamates, ascorbates, tartrates, salicylates, succinates, lactates, glutarates, gluconates, acetates, tricarballylates, citrates, fumarates and maleates) and, more particularly, inorganic base salts such as alkali metal salts (for example sodium salts).

By "a pharmaceutically acceptable derivative" is meant any pharmaceutically acceptable ester, ether or salt of such ester or ether of a compound of formula (I) or any other compound which, upon administration to a mammal, is capable of transformation (directly or undirectly) into a compound of formula (I) or an antivirally active metabolite or residue thereof.

Preferred esters of a compound of formula (I) include carboxylic acid esters in which the atom or group attached to the carbonyl moiety of the ester grouping is selected from hydrogen, straight or branched chain alkyl (e.g. methyl, ethyl, n-propyl, t-butyl, n-butyl), alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$alkyl or $C_{1-4}$alkoxy); sulphonate esters such as alkyl- or aralkylsulphonyl (e.g. methanesulphonyl); amino acid esters (e.g. L-valyl or L-isoleucyl) and mono-, di- or tri-phosphate esters.

Preferred ethers of a compound of formula (I) include straight or branched chain lower $C_{1-4}$ alkyl ethers such as isopropyl ethers.

With regard to the above described esters any alkyl moiety present advantageously contains 1 to 18 carbon atoms, particularly 1 to 4 carbon atoms. Any aryl moiety present in such esters advantageously comprises a phenyl group.

References hereinafter to a compound according to the invention includes both the compound of formula (I) and salts, solvates and pharmaceutically acceptable derivatives thereof.

The compound of formula (I) may exist in tautomeric forms, for example in the form

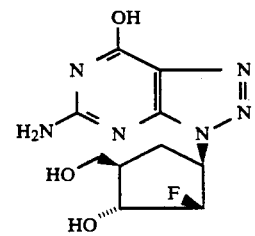

and it will be understood that all tautomeric forms of the compound of formula (I) are included within the scope of the invention.

It is to be understood that the present invention encompasses the individual enantiomers of the compound of formula (I) and its tautomers as well as wholly or partially racemic mixtures of such enantiomers, even though the precise structures as set out only relate to one enantiomer.

Particularly preferred, according to the invention, is (+)-5- amino-3,6-dihydro-3-[(1R,2R,3R,4R)-2-fluoro-3-hydroxy-4- (hydroxymethyl)cyclopentyl]-7H-1,2,3-triazolo[4,5-d]pyrimidin-7-one and its physiologically acceptable salts (e.g. the sodium salt) and solvates and pharmaceutically acceptable derivatives.

We have found that the compounds of the invention are highly potent in vitro and in vivo against strains of HSV-1, HSV-2 and VZV whilst having a low level of cytotoxicity. In vitro testing was carried out using the standard plaque reduction test whilst in vivo testing was carried out on the mouse according to the method described by Ericson et al. (1985) Antimicrobial Agents-Chemotherapy 27, 753–759.

It should be noted that the compounds of the invention lack a glycosidic bond which forms a site for both chemical and biological cleavage. Stability against glycosidic cleavage is, of course, a valuable feature in compounds for in vivo use.

In view of their antiviral activity, the compounds of the invention recommend themselves for the treatment of a variety of diseases caused by viruses, particularly primary and recurrent infections caused by the Herpetoviridae in human beings and animals, including diseases such as stomatitis, skin eruptions, chicken-pox, shingles, encephalitis, eye and genital herpes infections, retinitis and pneumonitis.

The present invention thus further includes a compound of formula (I) or a physiologically acceptable salt or solvate or a pharmaceutically acceptable derivative thereof for use in therapy for the treatment or prophylaxis of viral infections, especially Herpetoviridae (e.g. herpes simplex or VZV) infections, in a human or animal subject.

According to a further aspect of the invention there is provided the use of a compound of formula (I) or a physiologically acceptable salt or solvate or a pharmaceutically acceptable derivative thereof for the manufacture of a medicament for the treatment or prophylaxis of viral infections, especially Herpetoviridae (e.g. herpes simplex or VZV) infections, in a human or animal subject.

According to another aspect of the invention there is provided a method of treatment of a human or animal body to combat viral infections, especially Herpetoviridae (e.g. herpes simplex or VZV) infections, which method comprises administering to the said body a therapeutically effective amount of a compound of formula (I) or a physiologically acceptable salt or solvate or a pharmaceutically acceptable derivative thereof.

Compounds of the invention may be formulated for administration in any convenient way, and the invention therefore also includes within its scope pharmaceutical compositions for use in the treatment or prophylaxis of viral infections in a human or animal subject comprising at least one compound of formula (I) or a physiologically acceptable salt or solvate or a pharmaceutically acceptable derivative thereof together, if desirable, with one or more physiologically acceptable carriers or excipients.

Compounds of the invention may, for example, be formulated for oral, buccal, parenteral, topical or rectal administration.

Tablets and capsules for oral administration may contain conventional excipients such as binding agents, for example syrup, acacia, gelatin, sorbitol, tragacanth, mucilage of starch or polyvinyl pyrrolidone; fillers, for example, lactose, sugar, maize-starch, calcium phosphate or sorbitol; lubricants, for example, magnesium stearate, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for consitution with water or other suitable vehicle before use. Such liquid preparations may contain conventional additives (such as suspending agents), for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan monooleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic aid. The compound may also be formulated as suppositories, e.g. containing conventional suppository bases such as cocoa butter or other glycerides.

For buccal administration the compositions may take the form of tablets or lozenges formulated in conventional manner.

Compounds of the invention may also be formulated for injection and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as antioxidants, buffers, antimicrobial agents and/or toxicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

For topical administration compounds of the invention may be formulated as ointments, creams, lotions, powders, pessaries, sprays, aerosols or drops (e.g. eye or nose drops). Ointments and creams may, for example, be formulated with an aqueous or oily base with the addition of suitable thickening and/or gelling agents. Such bases may thus, for example, include water and/or an oil such as liquid paraffin or a vegetable oil such as arachis oil or castor oil. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Aerosol sprays are conveniently delivered from pressurised packs, with the use of a suitable propellant, e.g. dichlorodifluoromethane, trichlorofluoromethane, dichlorotetrafluoroethane, carbon dioxide or other suitable gas.

The pharmaceutical compositions according to the invention may also contain other active ingredients such as antimicrobial agents, or preservatives.

The compositions may contain from 0.1%–99% of the active material. For topical administration, for example, the composition will generally contain from 0.01% to 20%, more preferably 0.5% to 5% of the above material.

For topical administration the daily dosage as employed for adult human treatment will range from 0.1 mg to 1000 mg, preferably 0.5 mg to 10 mg. However, it will be appreciated that extensive skin infections may require the use of higher doses.

For systemic administration the daily dosage as employed for adult human treatment will range from 5 mg, to 5000 mg, preferably 50 mg to 2000 mg, which may be administered in 1 to 5 daily doses, for example, depending on the route of administration and the condition of the patient. When the compositions comprise dosage units, each unit will preferably contain 2 mg to 2000 mg of active ingredient, for example 50 mg to 500 mg. For serious infections the compounds may be administered by intravenous infusion using, for example 0.01 to 10 mg/kg/hr of the active ingredient.

Compounds of the invention may be administered in combination with one or more further therapeutic agents such as a different antiviral agent.

The invention thus provides, in a further aspect, a combination comprising a compound of formula (I) or a physiologically acceptable salt or solvate or a pharmaceutically acceptable derivative thereof together with another therapeutically active agent, in particular an antiviral agent.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention.

The individual components of such combinations may be administered either sequentially or simultaneously in separate or combined pharmaceutical formulations.

When a compound of the invention is used in combination with a second therapeutic agent active against the same virus the dose of each compound may differ from that when the compound is used alone. Appropriate doses will be readily appreciated by those skilled in the art.

According to another aspect of the invention we provide processes for the preparation of a compound of formula (I) or a salt, solvate or pharmaceutically acceptable derivative thereof. Thus one process (a) for the preparation of a compound of formula (I) or a salt, solvate or pharmaceutically acceptable derivative thereof comprises the step of converting the atom or group X in a compound of general formula (II)

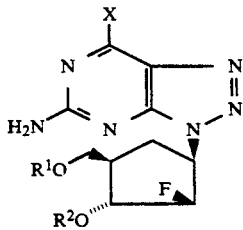

(II)

(wherein X represents an atom or a group convertible into a hydroxy group and $R^1$ and $R^2$, which may be the same or different, represent hydrogen atoms or protecting groups) or a salt thereof into a hydroxy group, followed, where necessary, by the removal of any protecting groups not required in the final product, with salt formation and conversion to a pharmaceutically acceptable derivative of a compound of formula (I) as optional subsequent steps.

The atom or group X may be, for example, an atom or group convertible by hydrolysis into a hydroxy group, such as a halogen atom (e.g. chlorine), $NH_2$, alkoxyamino (e.g. $CH_3ONH$-), benzyloxyamino or alkoxy (e.g. methoxy).

It will be appreciated that the resulting compound in which X is a hydroxy group is merely the tautomeric form of the compound of formula (I).

The hydrolysis reaction may be effected in an aqueous solvent such as water or a mixture of water and a water-miscible solvent such as an alcohol, e.g. methanol or ethanol, an ether, e.g. dioxan or tetrahydrofuran, a ketone, e.g. acetone, an amide, e.g. dimethylformamide or a sulphoxide, e.g. dimethylsulphoxide, conveniently in the presence of an acid or base.

Suitable acids which may be used in the above process according to the invention include organic acids, e.g. p-toluenesulphonic acid and inorganic acids, e.g. hydrochloric acid, nitric acid and sulphuric acid. In some cases (e.g. when hydrochloric acid is used) the acid may also be the reaction solvent.

Suitable bases which may be used in the above process according to the invention include inorganic bases, e.g. alkali metal hydroxides or carbonates such as sodium or potassium hydroxide or sodium or potassium carbonate.

The process is conveniently effected at a temperature in the range $-100°$ to $+150°$, e.g. $50°$ to $120°$ C.

The group X in formula (II) may also be converted to a hydroxyl group by enzyme-mediated hydrolysis. Thus, the hydrolysis may conveniently be effected by treating a compound of formula (II) with an enzyme such as adenosine deaminase in the presence of a phosphate buffer (e.g. sodium hydrogen phosphate). The reaction may conveniently take place at an elevated temperature (e.g. at about $40°$ C.). The enzyme-mediated hydrolysis is a convenient means of preparing an optically active compound of formula (I) from a racemate of formula (II).

Where $R^1$ and/or $R^2$ represents a protecting group, it may be any conventional hydroxyl protecting group, for example as described in 'Protective Groups in Organic Chemistry', Ed. J. F. W. McOmie (Plenum Press, 1973) or 'Protective Groups in Organic Synthesis' by Theodora W. Greene (John Wiley and Sons, 1981). Examples of suitable protecting groups include alkyl groups such as methoxymethyl; aralkyl groups such as benzyl, diphenylmethyl or triphenylmethyl; heterocyclic groups such as tetrahydropyranyl; acyl groups such as acetyl; and silyl groups such as trialkylsilyl groups, e.g. t-butyldimethylsilyl. $R^1$ and $R^2$ may also form a single protecting group, for example a tetraalkyldisilyloxy group such as 1,1,3,3-tetraisopropyldisilyloxy or a benzylidene group.

The protecting groups may be removed by using conventional techniques to yield a compound of formula (I). Thus an alkyl, aryl, silyl or heterocyclic group may, for example, be removed by solvolysis, e.g. hydrolysis under acidic or basic conditions, and an aralkyl group may be cleaved with a boron trihalide e.g. boron trichloride in a solvent such as methylene chloride and at low temperature. Where $R^1$ and $R^2$ together represent a tetraalkyldisilyloxy group, this may be removed by treatment with a tetraalkylammonium halide, e.g. tetra-n-butylammonium fluoride.

Another process (b) for the preparation of a compound of formula (I) or a salt, solvate or pharmaceutically acceptable derivative thereof comprises reacting a compound of formula (III)

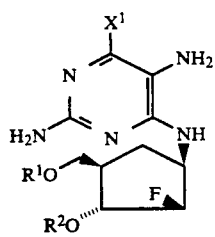

(wherein $R^1$ and $R^2$ are as defined previously and $X^1$ represents a hydroxy group or an atom or group X as defined previously) or a salt thereof with nitrous acid, followed where necessary by conversion of $X^1$ into a hydroxy group and by removal of any protecting groups not required in the final product, with salt formation and conversion to a pharmaceutically acceptable derivative of a compound of formula (I) as optional subsequent steps.

The reaction with nitrous acid may be conveniently effected by adding a solution of a nitrite, e.g. sodium nitrite, to an aqueous solution of a compound of formula (III) in the presence of an acid e.g. acetic acid, at a low temperature such as 0° C. Alternatively, the use of isoanyl nitrite in chloroform with a catalytic amount of acetic acid can be employed. The conversion of $X^1$ into a hydroxy group may be carried out under the conditions described in process (a) above and the removal of any protecting groups present may be effected as described above.

Intermediate compounds of formula (II) may be prepared by reacting compounds of formula (III) in which $R^1$ and $R^2$ are as defined previously and $X^1$ represents an atom or group X as defined previously, or a salt thereof with nitrous acid according to the method of process (b) above. Compounds of formula (II) may also be prepared from other compounds of formula (II) in which X represents a different atom or group convertible to a hydroxyl group by conventional anion exchange means.

A preferred method for the preparation of the (+) enantiomer of the compound of formula (I) (i.e. the compound (+)-5-amino-3,6-dihydro-3-[(1R,2R,3R,4R)-2-fluoro-3-hydroxy-4-(hydroxymethy)cyclopentyl]-7H-1,2,3-triazolo[4,5-d]pyrimidin-7-one) and its physiologically acceptable salts and solvates and pharmaceutically acceptable derivatives is from the appropriate enantiomer of formula (II) in which X represents alkoxyamino or, more preferably, benzyloxyamino and $R^1$ and $R^2$ represent hydrogen atoms under the conditions described in process (a) above. This compound of formula (II) may be prepared according to the following reaction sequence:

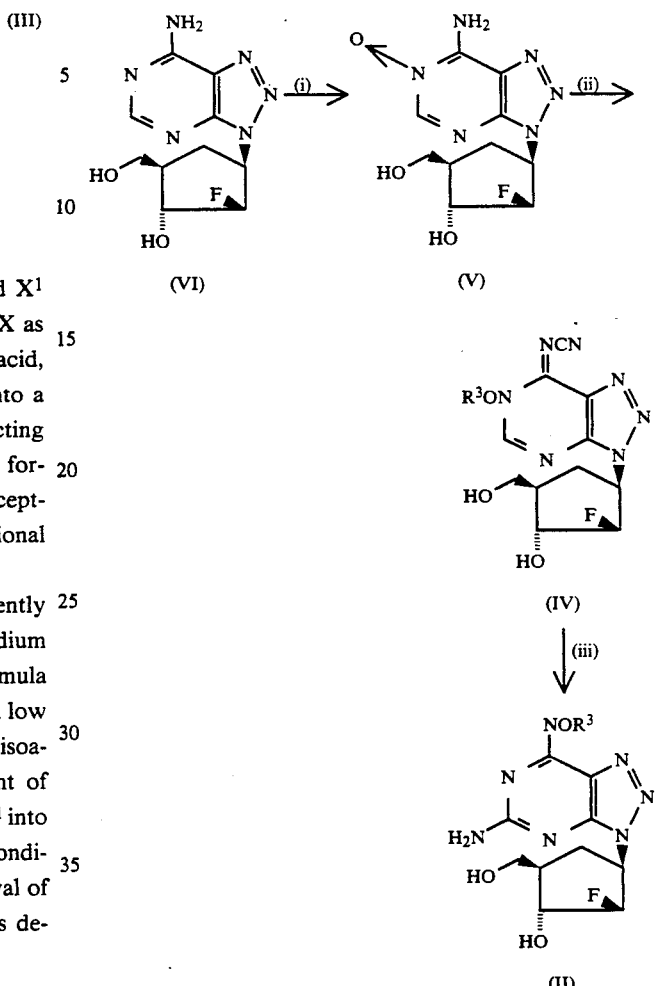

(where $R^3$ represents alkyl or benzyl)

Step (i) may be effected by oxidation, for example using a peracid such as mchloroperbenzoic acid in a solvent such as an aqueous ether (e.g. aqueous 1,4-dioxan). Step (ii) involves reacting the compound of formula (V) with cyanogen bromide in a solvent such as an alcohol (e.g. methanol) or an amide (e.g. dimethylformamide) at reduced temperature, e.g. −5° to 0° C., followed by treatment with an alcohol $R^3OH$ (where $R^3$ is as defined above) or an alkyl halide $R^3Hal$ (where Hal is a halogen atom such as bromine) and a suitable base such as a tertiary amine (e.g. triethylamine). Step (iii) may be effected by heating a compound of formula (IV) (e.g. at reflux) in a suitable solvent such as an alcohol (e.g. ethanol) and in the presence of a suitable base (e.g. 1,8-diazabicyclo[5.4.0]undec-7-ene).

The compound of formula (VI) may be prepared from aristeromycin according to either of reaction sequences (a) or (b) below:

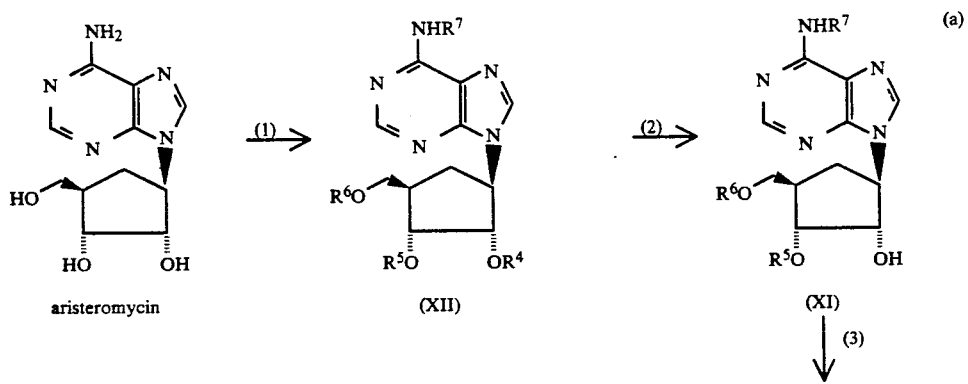
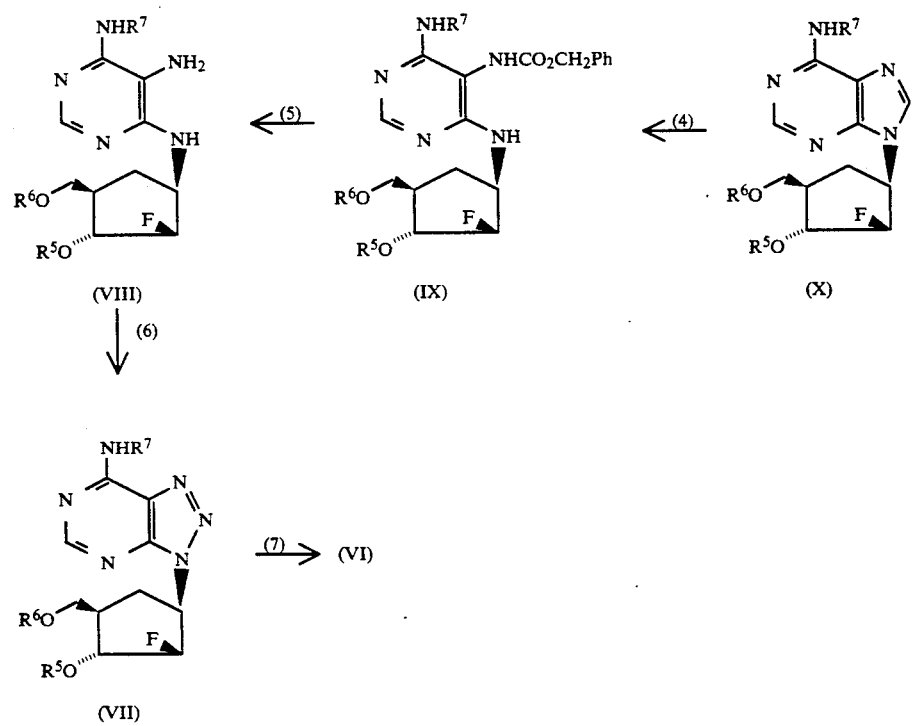
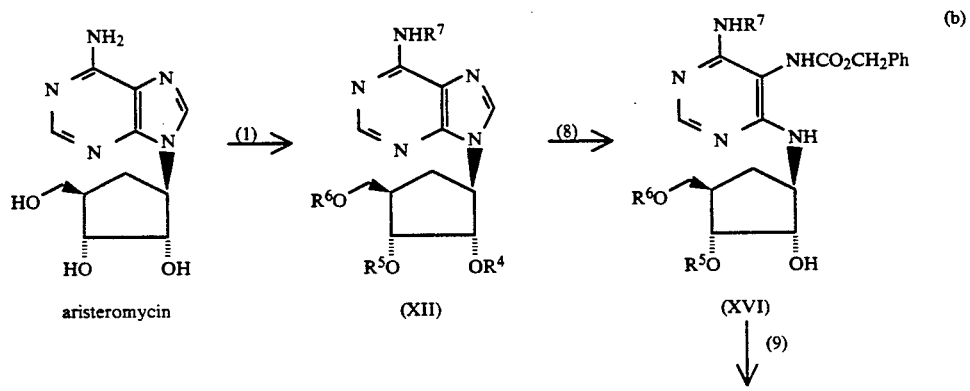

-continued

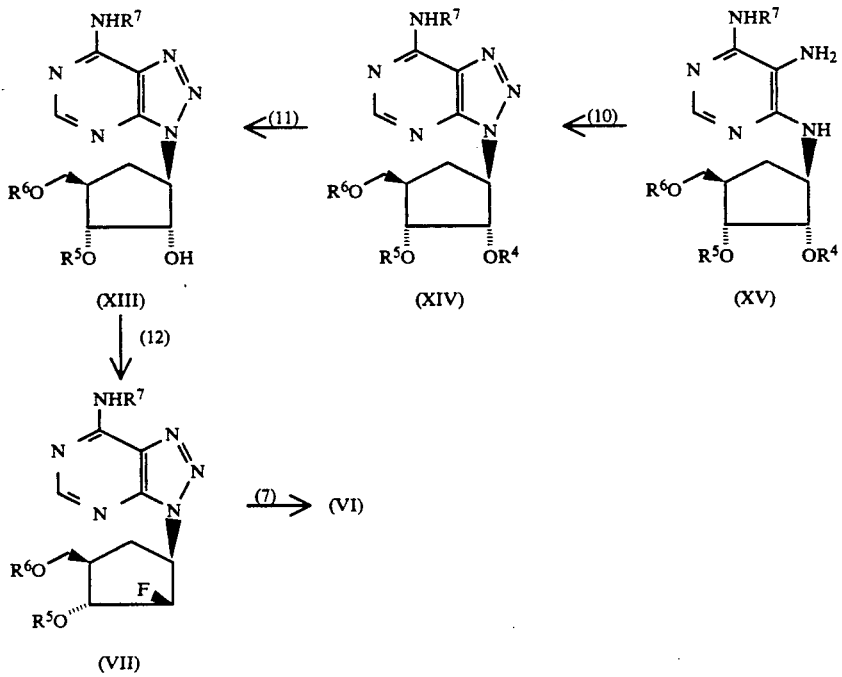

(XIII)　　　　　(XIV)　　　　　(XV)

In reaction sequences (a) and (b) above, $R^4$-$R^7$ represent suitable hydroxyl and amine protecting groups, for example as described in 'Protective Groups in Organic Chemistry', Ed. J.F. W. McOmie (Plenum Press, 1973) or 'Protective Groups in Organic Synthesis' by Theodora W. Greene (John Wiley and Sons, 1981). Examples of suitable protecting groups include acyl groups such as benzoyl.

Step (1) may be effected by conventional means. Thus, for example, when $R^4$-$R^7$ each represents a benzoyl group the protecting groups may be introduced by reacting aristeromycin with benzoyl chloride in the presence of pyridine.

Step (2) may be effected by treating the compound of formula (XII) with a strong base such as potassium tert-butoxide in an ether solvent (e.g. tetrahydrofuran) at low temperature (e.g. about $-40°$ C.).

Step (3) may be effected by treating the compound of formula (XI) with a fluorinating agent. Suitable fluorinating agents include diethylaminosulphur trifluoride or diethyl-(2-chloro-1,1,2-trifluoroethyl)amine. The reaction is conveniently effected in an inert solvent such as a halogenated hydrocarbon such as dichloromethane or chloroform or an ether (e.g. tetrahydrofuran) and at a temperature of for example $-70°$ to $0°$ C.

Step (4) involves reacting a compound of formula (X) with dibenzyl pyrocarbonate in an ether solvent such as tetrahydrofuran, optionally in the presence of water and conveniently at ambient temperature.

Step (5) may be effected by hydrogenolysis and decarboxylation of a compound of formula (IX) using hydrogen in the presence of a suitable catalyst such as palladium-on-carbon and in a solvent such as ethyl acetate.

Step (6) may be effected according to the procedure outlined in general process (b) above.

Step (7) may be effected by standard deprotection means. Thus, for example, when $R^5$-$R^7$ each represents a benzoyl group the protecting groups may be conveniently removed by treating the compound of formula (VII) with a base such as an alkali metal alkoxide (e.g. sodium methoxide) in an alcoholic solvent (e.g. methanol), conveniently at ambient temperature.

Steps (8), (9), (10), (11) and (12) may be carried out under the general conditions described above for steps (4), (5), (6), (2) and (3) respectively.

The compounds of formula (III) are either known compounds described in UK Patent Specification No. 2179349A or may be prepared from the known compounds of formula (III) by conventional means.

Compounds of formulae (II), (IV), (V), (VI), (VII), (VIII), (IX), (XIII), (XIV), (XV) and (XVI) are novel intermediates and form further aspects of the present invention. The compound of formula (VI) represent a key intermediate in the synthesis of (+)-5-amino-3,6-dihydro-3-[(1R,2R,3R,4R)-2-fluoro-3-hydroxy-4-(hydroxymethyl)cyclopentyl]-7H-1,2,3-triazolo[4,5-d]pyrimidin-7-one.

When it is desired to prepare an acid addition salt of a compound of formula (I) the product of any of the above procedures may be converted into a salt by treatment of the resulting free base with a suitable acid using conventional methods.

Physiologically acceptable acid addition salts of the compound of formula (I) may be prepared by reacting a compound of formula (I) in the form of the free base with an appropriate acid optionally in the presence of a suitable solvent such as an ester (e.g. ethyl acetate) or an alcohol (e.g. methanol, ethanol or isopropanol).

Inorganic basic salts may be prepared by reacting the free base of a compound of formula (I) with a suitable base e.g. an alkoxide such as sodium methoxide optionally in the presence of a solvent (e.g. an alcohol such as methanol).

Physiologically acceptable salts may also be prepared from other salts, including other physiologically acceptable salts, of the compound of formula (I) using conventional methods.

The compound of formula (I) may be converted into a pharmaceutically acceptable derivative thereof by conventional means. Thus, for example, a pharmaceutically acceptable phosphate or other ester may be prepared by reacting a compound of formula (I) with a phosphorylating agent, such as POCl$_3$, or a suitable esterifying agent, such as an acid halide or anhydride, as appropriate.

Solvates (e.g. hydrates) of a compound of formula (I) may be formed during the work-up procedure of one of the aforementioned process steps.

The following Preparations and Examples illustrate the invention but should not be construed as a limitation thereof. All temperatures are in °C.

INTERMEDIATE 1

(±)(1α,2β,3α,4β)-4-[(2,5-Diamino-4-chloro-6-pyrimidinyl)amino]-3-fluoro-2-hydroxycyclopentanemethanol Intermediate 6 in UK Patent Specification No. 2179349A.

INTERMEDIATE 2

(±)(1α,2β,3α,4α)-4-(5-Amino-7-chloro-3H-1,2,3-triazolo[4,5-d]-pyrimidin-3-yl)-3-fluoro-2-hydroxycyclopentanemethanol A solution of sodium nitrite (145 mg) in water (3 ml) was added dropwise to a stirred and cooled (0°) solution of Intermediate 1 (530 mg) in water (5 ml) and glacial acetic acid (1.67 ml). After a further 30 min at 0° the precipitate was collected, washed with ice-water and dried in vacuo to give the title compound as a white solid (473 mg); m.p. 103°-106° (Kofler), $\lambda_{max}$(ethanol) 226 nm (E 780), 315 nm (E 780), 315 nm (E 225).

INTERMEDIATE 3

(1R,2R,3R,4R) N-[9-[3-(Benzoyloxy)-4-[(benzyloxy)-methyl]-2-fluorocyclopentyl]-9H-purine-6-yl]benzamide (cf. K. Biggadike et al., *J. Chem. Soc. Chem. Commun.* 1988, 899).

INTERMEDIATE 4

(1R,2R,3R,4R)
2-[2-[(3-Benzoyloxy)-4-[(benzyloxy)methyl]-2-fluorocyclopentyl]amino]-4-(benzoylamino)pyrimidin-3-yl]carbamic acid phenyl methyl ester Dibenzyl pyrocarbonate (30.7 g) and Intermediate 3 (28.45 g) in tetrahydrofuran (1.51) and water (375 ml) was stirred at ambient temperature for 60 h. Sodium hydrogen phosphate buffer (pH 7.0, 0.5M 1.71) was added and the product extracted into ethyl acetate (3×500 ml). The combined extracts were dried (MgSO$_4$) and evaporated to a brown oil. This oil was subjected to chromatography on silica (1 kg, Merck 9385), eluted with cyclohexane/ethyl acetate/acetic acid (30:30:1) mixtures to afford the title compound (24.59 g) as a colourless foam; $[\alpha]_d^{20}$ −10.0° (C1.48, CHCl$_3$), $\nu_{max}$(CHBr$_3$) 3300-3200, 1720, 1675, 1600, 1582 cm$^{-1}$.

INTERMEDIATE 5

(1R,2R,3R,4R)
N-[6-[[3-(Benzoyloxy)-4-[(benzoyloxy)methyl]-2-fluorocyclopentyl]amino]-5-aminopyrimidin-6-yl]benzamide To a solution of Intermediate 4 (8.85 g) in ethyl acetate (25 ml) and ethanol (480 ml) was added 10% palladium on carbon catalyst (2.99 g). Hydrogen was bubbled through this mixture at ambient temperature for 28 h. More catalyst (0.75 g) was added and the reaction continued for 19 h. The mixture was filtered through keiselghur and evaporated to afford the title compound (6.50 g);
$[\alpha]_D^{20}$ −29.28°(c 0.87, CHCl$_3$), $\lambda_{max}$(EtOH) 229.4 nm (E 720), 307.0 nm (E 151)nm; $\nu_{max}$(nujol) 3394, 1718, 1676, 1600, 1581 cm$^{-1}$.

INTERMEDIATE 6

(1R,2R,3R,4R)
N-[3-[3-(Benzoyloxy)-4-[(benzoyloxy)methyl]-2-fluorocyclopentyl]-3H-1,2,3-triazolo[4,5-d]pyrimidin-7-yl]benzamide (i) Sodium nitrite (0.63 g) in water (20.7 ml) was added to an aqueous solution of Intermediate 5 (4.45 g). Acetic acid (7.1 ml) was added dropwise to the above solution at 0° over 0.18 h, then the mixture stirred for 4 h between 0°-22°. The mixture was partitioned between ethyl acetate and water, the organic phase separated and washed with aqueous sodium hydrogen carbonate and brine. Evaporation afforded a brown foam which was subjected to chromatography on silica (Merck 7734), eluted with ethyl acetate/cyclohexane (3:1) mixtures to give the title compound (2.19 g) as a colourless foam; $[\alpha]_D^{20}$ −23.91° (c 1.02, CHCl$_3$), $\lambda$ max (EtOH) 228.6 nm (E 587), 281.2 nm (E 362) nm, $\nu_{max}$(nujol) 3300,1720,1599 cm$^{-1}$.

(ii) A mixture of the Intermediate 5 (10.26 g),isoamyl nitrite (2.53 g) and acetic acid (68 mg) in chloroform (200 ml) was stirred at reflux for 1.42 h. The solvent was evaporated and the residue partitioned between ethyl acetate and sodium hydrogen carbonate solution. The organic phase was evaporated to yield a grey foam (10.25 g). This material was subjected to chromatography (Merck 7734, 120 g), eluted with ethyl acetate/cyclohexane (3:1) mixtures to yield the title compound as a light brown foam (5.53 g). Spectral data ($^1$H nmr and IR) of this material was identical to that of the compound prepared by method (i).

INTERMEDIATE 7

(1R,2R,3R,4R)
4-[7-Amino-3H-1,2,3-triazolo[4,5-d]pyrimidin-3-yl]-3-fluoro-2-hydroxy cyclopentanemethanol To a solution of Intermediate 6 (3.1 g) in tetrahydrofuran (10 ml) and methanol (30 ml) was added a solution of sodium methoxide in methanol (1%, 78.1 ml). The reaction mixture was stirred at ambient temperature for 24 h. DOWEX 50 W-X8 resin (ca 25 ml) was added and stirring continued for 0.25h. After filtration, the liquor was evaporated to give a product which was crystallized from methanol (3 ml) to afford the title compound (0.25 g); m.p. 214–216°, $[\alpha]_D^{20}$ +94.69°(c 0.97, dimethylsulphoxide).

INTERMEDIATE 8

(1R,2R,3R,4R)
4-[7-Amino-3H-1,2,3-triazolo[4,5-d]pyrimidin-3-yl]-3-fluoro-2-hydroxycyclopentanemethanol, 6-oxide A solution of Intermediate 7 (324 mg) and 80–90% meta-chloroperoxybenzoic acid (396 mg) in 1,4 dioxan (6 ml) and water (6 ml) was stirred at ambient temperature for 72 h. Evaporation gave a residue which was boiled with ether, then methanol, and collected by filtration to afford the title compound (222 mg) as a colourless solid; m.p. 260-264° (dec), $[\alpha]_D^{20}$ +97.86°(c.0.99, dimethylsulphoxide).

INTERMEDIATE 9

[3-[2-Fluoro-3-hydroxy-4-(hydroxymethyl)cyclopentyl]-6-[(phenylmethyl)oxy]-1,2,3-triazolo[4,5-d]pyrimidin-7-yl]cyanamide To a suspension of Intermediate 8 (225 mg) in dimethylformamide (2 ml) at 0° was added a solution of cyanogen bromide (98 mg) in dimethylformamide (0.6 ml). After stirring at 0° for 1 h and at 22° for 2 h the mixture was recooled to 0°. Benzyl bromide (280 μl) was added followed by triethylamine (0.33 ml). The mixture was stirred for 2.6 h, and then the solvents evaporated. The residue was subjected to chromatography over silica (40 g, Merck, 7734), eluted with dichloromethane/methanol mixtures to afford the title compound (307 mg) as a brown gum; $^1$H n.m.r. (DMSO-d$_6$) δ 9.17 (1H), 7.7 (5H), 5.70 (1H), 5.51 (2H), 5.50 (1H), 5.19 (1H), 4.98 (1H), 4.22 3.75 (2H), 2.55 (2H), 2.20 (1H).

INTERMEDIATE 10

(1R,2R,3R,4R) 4-[5-Amino-7-[(phenylmethoxy)amino]-3H-1,2,3-triazolo[4,5-d]pyrimidin-3-yl]-3-fluoro-2-hydroxycyclopentanemethanol A suspension of Intermediate 9 (294 mg) in ethanol (4.9 ml), 1,8-diazabicyclo [5,4,0]undec-7-ene (56 mg) and water (49 μl) was heated at reflux for 3 h. The solvent was evaporated and the residue triturated with chloroform to afford the title compound (164 mg); $^1$H n.m.r. (DMSO-d$_6$) δ 10.07 (1H), 7.4 (5H), 7.05 (2H), 5.40 (1H), 5.09 (2H), 4.92 (1H), 4.86 (1H), 4.24 (1H), 4.02 (1H), 3.49 (2H), 2.36 (1H), 1.94 (1H), 1.62 (1H).

INTERMEDIATE 11

(1R,2S,3R,4R)-2-[2-[[2,3-Bis[(benzoyloxy)]-4-[(benzoyloxy)methyl]cyclopentyl]amino]-4-(benzoylamino)-pyrimidin-3-yl]carbamic acid phenyl methyl ester A solution of (1R,2S,3R,4R)-N-[9-[2,3-bis[(benzyloxy)]-4-(benzyloxy)methyl]cyclopentyl]-9H-purin-6-yl]benzamide (1.0 g; J. Chem. Soc. Chem. Commun., 1988, 898-900) and dibenzyl pyrocarbonate (0.842 g) in tetrahydrofuran (44 ml) and water (11 ml) was stirred at ambient temperature for 24 h. Sodium hydrogen phosphate buffer (pH 7.00, 0.5M, 20 ml) was added and the products extracted with ethyl acetate. The extract was dried (MgSO$_4$) and evaporated to yield a colourless syrup (1.89 g). This was subjected to chromatography over silica (Merck 7734, 100 g), eluted with ethyl acetate/diethyl ether (1:2) to afford a gum (1.62 g). This material was triturated with isopropyl ether to afford the title compound as a colourless solid (0.98 g); m.p. 94°-99°(with softening from 60°), $[\alpha]_D^{20}$ −90.31°(c 1.01, CHCl$_3$); $^1$H n.m.r. (DMSO-d$_6$) δ 10.63 (1H), 8.29 (1H), 8.00-7.1 (27H), 5.64 (2H), 5.05 (3H), 4.50 (2H), 2.90 (1H), 2.50 (1H), 1.71 (1H).

INTERMEDIATE 12

(1R,2S,3R,4R) N-[6-[[2,3-Bis[(benzoyloxy)]-4-[(benzoyloxy)methyl]-cyclopentyl]amino]-5-aminopyrimidin-6-yl]benzamide A solution of Intermediate 11 (4.25 g) in ethanol (400 ml) was hydrogenated over 10% palladium/carbon catalyst (4.0 g) for 18 h at ambient temperature. The catalyst was separated by filtration through keiselghur. Evaporation of the filtrate afforded the title compound (3.37 g) as a yellow/green foam; m.p. (foam) 100°-108°, $[\alpha]_D^{20}$ −115.27°(c 1.01, CHCl$_3$); $^1$H n.m.r. (DMSO-d$_6$) δ 10.4 (1H), 7.87 (1H), 8.1-7.3 (20H), 7.10 (1H), 5.66 (1H), 5.57 (1H), 4.90 (1H), 4.59 (2H), 4.52 (2H), 2.92 (1H), 2.69 (1H), 1.65 (1H).

INTERMEDIATE 13

(1R, 2S,3R,4R) N-[3-[2,3-Bis[(benzoyloxy)]-4-[(benzoyloxy)methyl]cyclopentyl]-3H-1,2,3-triazolo[4,5-d]pyrimidin-7-yl]benzamide To a solution of Intermediate 12 (3.37 g) in tetrahydrofuran (37.5 ml) at 0° was added, with stirring, sodium nitrite (403 mg) in water (14 ml) followed by acetic acid (4.6 ml, in five portions over 20 min). The reaction was stirred at ambient temperature for 1.75 h. The mixture was partitioned between ethyl acetate and aqueous sodium hydrogen carbonate. The organic extract evaporated to give a brown foam (3.19 g). This material was subjected to chromatography over silica (Merck 7734, 150 g), eluted with ethyl acetate/cyclohexane (1:1) to yield the title compound as a yellow foam (1.83 g); m.p. (foam) 98°-103°, $[\alpha]_D^{20}$ −114.9°(c 1.06, CHCl$_3$), $^1$H n.m.r. (DMSO-d$_6$) δ 12.00 (1H), 8.85 (1H), 8.15-7.3 (20H), 6.14 (1H), 5.90 (2H), 4.65 (2H), 3.19 (1H), 2.90 (1H), 2.60 (1H).

INTERMEDIATE 14

(1R,2S,3R,4R) N-[3-[3-(Benzoyloxy)-4-[(benzoyloxy)methyl]-2-hydroxy cyclopentyl]-3H-1,2,3-triazolo[4,5-d]pyrimidin-7-yl]benzamide Potassium t-butoxide (4.38 g) in tetrahydrofuran (90 ml) was added over 0.5 h to a solution of Intermediate 13 (7.60 g) in tetrahydrofuran (24 ml) maintained at −50°. After addition, the bright blue solution was stirred at −40° to −30° for 2 h. After recooling to −50°, a mixture of dichloromethane and sodium hydrogen phosphate buffer (0.5M, pH7.00) was added. The organic extract was evaporated to yield a brown foam (5.81 g). This material was subjected to chromatography over silica (Merck 7734, 400 g), eluted with ethyl acetate/cyclohexane to afford the title compound (4.77 g) as a pale yellow foam; m.p. (foam) 108°-118°, $[\alpha]_D^{20}$ −78.06°(c 1.06, CHCl$_3$), $^1$H NMR (DMSO-d$_6$) δ 12.00 (1H), 8.85 (1H), 8.15-7.45 (15H), 5.75 (1H), 5.50 (1H), 5.44 (1H), 4.95 (1H), 4.55 (2H), 2.92 (1H), 2.70 (1H), 2.33 (1H).

INTERMEDIATE 15

(1R,2R,3R,4R) N-[3-[3-(Benzoyloxy)-4-[(benzoyloxy)methyl-2-fluorocyclopentyl]-3H-1,2,3-triazolo[4,5-d]pyrimidin-7-yl]benzamide To a solution of diethylaminosulphur trifluoride (2.27 ml) in dichloromethane (85 ml) and pyridine (3.95 ml) was added Intermediate 14 (4.68 g) in dichloromethane (188 ml) over 1 h at ambient temperature. The reaction was stirred for a further 96 h before the addition of cold, saturated sodium hydrogen carbonate solution (ca 100 ml). After 0.5 h, the organic phase was separated to yield a brown gum (5.68 g). The gum was subjected to chromatography over silica (Merck 7734, 300 g), eluted with ethyl acetate/cyclohexane (3:1), to yeild the title compound (2.16 g) as a light yellow foam;

$[\alpha]_D^{20}$ −25.77°(c 1.09, CHCl$_3$). Spectral data (UV and IR) on this product was identical to the material prepared by the previously described method of Intermediate 6.

EXAMPLE 1

(±)-5-Amino-3,6-dihydro-3-[(1α,2α,3β,4α)-2-fluoro-3-hydroxy-4-(hydroxymethyl)cyclopentyl]-7H-1,2,3-triazole[4,5-d]pyrimidin-7-one Intermediate 2 (220 mg) was suspended in 0.5N hydrochloric acid (8 ml) and the mixture was heated under reflux for 75 min and then cooled in ice. The precipitated product was collected, washed with ice-water and dried in vacuo to give the title compound as white crystals; m.p. 254°-256°, $\lambda_{max}$(H$_2$O) 253.5 nm (E 433), $^1$H n.m.r. (DMSO-d$_6$) δ 10.94 (1H), 6.90 (2H), 5.39 (1H), 5.03 (1H), 4.95 (1H), 4.70 (1H), 4.07 (1H), 3.44–3.65 (2H), 2.43 (2H) and 2.03 (1H).

EXAMPLE 2

(±)-5-Amino-3,6-dihydro-3-[(1α,2α,3β,4α)-2-fluoro-3-hydroxy-4-(hydroxymethyl)cyclopentyl]-7H-1,2,3-triazolo[4,5-d]pyrimidin-7-one, sodium salt 1N-Sodium hydroxide solution (0.61 ml) was added to a stirred suspension of the product of Example 1 (175 mg) in water (3 ml). The resulting solution was freeze-dried to give the title compound as a white amorphous solid (193 mg), $^1$H n.m.r. (DMSO-d$_6$) δ 5.54 (2H), 5.38 (1H), 4.7–5.0 (3H), 4.04 (1H), 3.4–3.65 (2H), 2.34 (2H) and 1.97 (1H).

Analysis Found C,36.45; H,4.39; N,25.24. C$_{10}$H$_{12}$FN$_6$NaO$_3$ requires C,36.24; H,4.50; N,25.36%.

EXAMPLE 3

(+)-5-Amino-3,6-dihydro-3-[(1R,2R,3R,4R)-2-fluoro-3-hydroxy-4-(hydroxymethyl)cyclopentyl]-7H-1,2,3-triazolo[4,5-d]pyrimidin-7-one Intermediate 2 (4.26 g) was added to sodium hydrogen phosphate buffer (0.1M, pH7, 540 ml) and sonicated and warmed to 50° to dissolve the solid. The mixture was filtered to separate a small quantity of insoluble material. The filtrate was cooled to 40° and adenosine deaminase (9.00 ml of an aqueous suspension containing ca 0.09 g enzyme) added. The mixture was stirred and maintained at 40° for 29h. The reaction mixture was filtered and the filtrate extracted with ethyl acetate (4×125 ml). The combined aqueous phases were freeze dried to afford a colourless solid. Multiple crystallisations from water affored the title compound in two batches. The first batch (0.56 g) was obtained as a colourless solid; m.p. 251°–55°(dec), $[\alpha]_D^{20}$+97.07°(c 0.958, H$_2$O).

Analysis Found: C,38.86; H,4.51; N,28.04. C$_{10}$H$_{13}$FN$_6$O$_3$:NaH$_2$PO$_4$:H$_2$O (7:1:2) requires: C,39.18; H,4.56; N,27.42%.

EXAMPLE 4

(+)-5-Amino-3,6-dihydro-3-[(1R,2R,3R,4R)-2-fluoro-3-hydroxy-4-(hydroxymethyl)cyclopentyl]-7H-1,2,3-triazolo[4,5-d]pyrimidin-7-one sodium salt The product of Example 3 (0.54 g) was dissolved in distilled water (30 ml) and 1M-sodium hydroxide (1.78 ml) added. The clear pale yellow solution was freeze-dried to afford the title compound (0.59 g), as a very pale yellow solid; $[\alpha]_D^{20}$+80.00°(c 1,H$_2$O).

Analysis Found: C,34.39; H,4.08; N,24.12; F,5.8 C$_{10}$H$_{12}$FN$_6$NaO$_3$:NaH$_2$PO$_4$:H$_2$O (6:1:1) requires: C,34.59; H,4.26; N,24.20; F,5.47%.

EXAMPLE 5

(+)-5-Amino-3,6-dihydro-3-[(1R,2R,3R,4R)-2-fluoro-3-hydroxy-4-(hydroxymethyl)cyclopentyl]-7H-1,2,3-triazolo[4,5-d]pyrimidin-7-one A suspension of Intermediate 10 (0.31 g) in 2M hydrochloric acid (5 ml) was heated at 125° for 2.5 h. On cooling, the mixture was neutralized with sodium hydrogen carbonate and then filtered through a charcoal column (3 g) eluting with water, then ethanol/water/0.88 ammonia (10:10:1) mixtures to afford the title compound as a pale brown solid (72 mg), $^1$H n.m.r. (DMSO-d$_6$) δ 9.70 (1H), 7.05 (2H), 5.41 (1H), 4.90 (1H), 4.03 (1H), 3.55 (2H), 2.40 (2H), 1.99 (1H).

EXAMPLE 6

Pharmaceutical compositions (1) Topical creams

| | % w/v |
|---|---|
| a) Active ingredient | 0.25 |
| b) Butylene glycol | 15.0 |
| c) Glycerol | 2.5 |
| d) Cetostearyl alcohol | 10.0 |
| e) Self emulsifying monostearin | 1.5 |
| f) Polyoxyethylene (2) olelyl ether | 5.0 |
| g) Beeswax | 3.0 |
| h) Chlorocresol | 0.1 |
| Distilled water to | 100.0 |

Heat the water to 70° and dissolve the chlorocresol (h). Melt (d), (e), (f) and (g) together, heating to 70°. Add the melt to the water with stirring. Disperse (a) in a mixture of (b) and (c) and add the dispersion (warmed to 55°) to the bulk mixture. Cool, with stirring, to 35°.

(2) Eye Ointment

| | % w/v |
|---|---|
| Active ingredient | 3.0 |
| Liquid paraffin | 25.00 |
| White soft paraffin to | 100.0 |

Melt the white soft paraffin by heating to 70°. Disperse the active ingredient in the liquid paraffin, warm the dispersion to 55° and add it with stirring to the molten white soft paraffin. Cool, with stirring, to 35°.

(3) Eye Drops

| | % w/v |
|---|---|
| Active ingredient | 0.5 |
| Benzalkonium chloride | 0.01 |
| Sodium chloride | 0.85 |
| Sodium citrate | 0.05 |
| Citric acid | 95 to pH 5.0 |
| Water for injections to | 100.0 |

Dissolve the benzalkonium chloride and sodium citrate in 90% of the water and disperse the active ingredient in the solution. Dissolve the citric acid in 5% of the water and add it to the suspension of the active ingredient. Stir until the active ingredient has dissolved. Add and dissolve the sodium chloride and make the solution up to volume with water. Filter the solution, collect the filtrate aseptically and fill (aseptically) into suitable sterile eye drop containers.

(4a) Oral Tablet

|  | mg/Tablet | % w/w |
| --- | --- | --- |
| Active ingredient | 100 | 38.3 |
| Lactose | 100 | 38.3 |
| Maize Starch | 50 | 19.2 |
| Polyvinyl pyrrolidone | 2 | 0.75 |
| Sodium starch glycolate | 7 | 2.7 |
| Magnesium stearate | 2 | 0.75 |

Sieve the active ingredient and maize starch through a 40 mesh screen. Blend the maize starch with the active ingredient in a suitable blender. Make an aqueous solution of the polyvinyl pyrrolidone in a 5–10% w/v solution. Add this solution to the mixing powders and mix until granulated. Using suitable equipment pass the granulate through a 12 mesh screen. Dry the granules in an oven or in a fluid bed dryer. Screen the dry granules through a 16 mesh screen, and blend in the sodium starch glycolate and magnesium stearate previously sieved through a 60 mesh screen. Compress on appropriate punches on an automatic tablet machine. The tablets may be covered in a thin polymer coat applied by the usual film coating techniques. A pigment may be included in the film coat.

(4b) Oral Tablet

|  | mg/tablet | % w/w |
| --- | --- | --- |
| Active ingredient | 100 | 33.3 |
| Microcrystalline cellulose | 192 | 64.0 |
| Sodium starch glycolate | 6 | 2.0 |
| Magnesium stearate | 2 | 0.7 |

Sieve the active ingredient and microcrystalline cellulose through a 40 mesh screen. Sieve the sodium starch glycolate and magnesium stearate through a 60 mesh screen. Blend the powders together in a suitable blender until homogenous. Compress on appropriate punches on an automatic tablet machine. The tablets may be covered in a thin polymer coat applied by the usual film coating techniques. A pigment may be included in the film coat.

(5) Oral Capsule

|  | mg/capsule | % w/w |
| --- | --- | --- |
| Active ingredient | 100 | 40.0 |
| Lactose anhydrous | 135 | 54.0 |
| Magnesium stearate | 2 | 0.8 |
| Sodium starch glycolate | 13 | 5.2 |

Sieve all the ingredients and mix in a suitable blender. Fill into suitable size hard gelatin capsules using an automatic capsule filling machine.

(6) Oral syrup

|  | % w/v |
| --- | --- |
| Active ingredient | up to 1.0 |
| Sucrose | 60.0 |
| Citrate buffer | as required to pH 4.0 |
| Methyl hydroxybenaoate | 0.15 |
| Propyl hydroxybenzoate | 0.02 |
| Colour (optional) | as required |
| Flavour (optional) | as required |

-continued

|  | % w/v |
| --- | --- |
| Distilled water to | 100.0 |

Dissolve the sucrose and hydroxybenzoates in water with the aid of heat. Cool and dissolve the buffer, the active ingredient and other items. Check the pH, adjust if necessary and then make up to volume. Fill the solution into suitable syrup containers.

(7) Oral suspension

|  | % w/v |
| --- | --- |
| Active ingredient | up to 5.0 |
| Sorbitan mono-oleate | 1.0 |
| Sucrose | 60.0 |
| Carboxymethyl cellulose | 3.0 |
| Methyl hydroxybenzoate | 0.15 |
| Propyl hydroxybenzoate | 0.02 |
| Citrate buffer | as required to pH 7.0 |
| Colour (optional) | as required |
| Flavour (optional) | as required |
| Distilled water to | 100.0 |

Dissolve the sucrose and hydroxybenzoates in most of the water with the aid of heat. Cool and disperse the carboxymethyl cellulose in part of the water with stirring. Mix the syrup and carboxymethyl cellulose gel. Dissolve the sorbitan mono-oleate and buffer in the dispersion, with stirring. Disperse the finely divided active ingredient in the resultant mixture. Add the colour and flavour as required. Check the pH and adjust if necessary. Make the mixture to volume and fill into suitable suspension containers.

(8) Powder (for external application)

|  | % w/w |
| --- | --- |
| Active ingredient | 3.0 |
| Silicon dioxide | 2.0 |
| Maize starch to | 100.0 |

Blend the sieved active ingredient, silicon dioxide and the maize starch in a suitable mechanical blender. Fill the resultant powder blend into suitable powder containers.

In the above pharmaceutical examples the active ingredient is (+)-5-amino-3,6-dihydro-3-[(1R,2R,3R,4R)-2-fluoro-3-hydroxy-4-(hydroxymethyl)cyclopentyl]-7H-1,2,3-triazolo[4,5-d]pyrimidin-7-one. Other compounds of the invention may be formulated in a similar manner.

We claim:

1. A compound of formula (I)

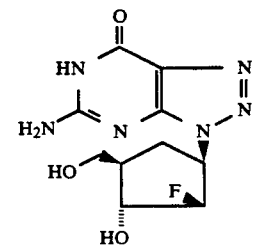

and physiologically acceptable salts and solvates thereof.

2. (+)-5-Amino-3,6-dihydro-3-[(1R,2R,3R,4R)-2-fluoro-3-hydroxy-4-(hydroxymethyl)cyclopentyl]-7H-1,2,3-triazolo[4,5-d]pyrimidin-7-one and its physiologically acceptable salts and solvates.

3. A method of treatment of a living human or animal body to combat Herpetoviridae infections, which method comprises administering to the said body a therapeutically effective amount of a compound of formula (I) as defined in claim 1 or a physiologically acceptable salt or solvate thereof.

4. Pharmaceutical compositions for use in the treatment or prophylaxis of viral infections in a human or animal subject comprising at least one compound of formula (I) as defined in claim 1 or a physiologically acceptable salt or solvate thereof in association with one or more pharmaceutical carries or excipients.

5. Compositions according to claim 4 formulated for oral, buccal, parenteral, topical or rectal administration.

6. Compositions according to claim 5 in the form of dosage units.

7. The compound of formula (VI)

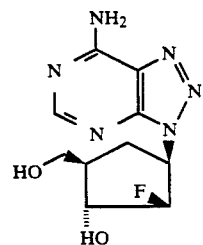

(VI)

8. Compounds of formula (II)

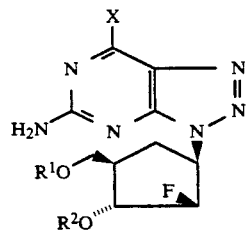

(II)

wherein X represents an atom or group convertible into a hydroxyl group and $R^1$ and $R^2$, which may be the same or different, each represents a hydrogen atom or a protecting group.

9. The compounds of formula (IV), (V), (VII), (XIII) or (XIV):

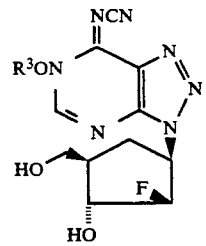

(IV)

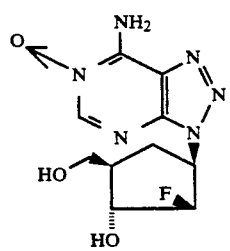

(V)

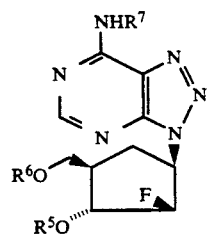

(VII)

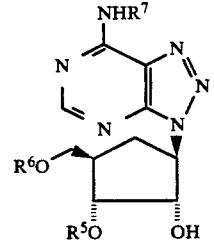

(XIII)

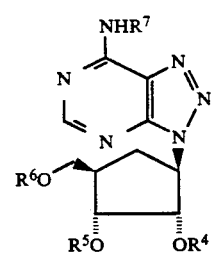

(XIV)

where $R^3$ represents alkyl or benzyl; and $R^4$–$R^7$ represent hydroxyl or amine protecting groups.